United States Patent [19]

Glattly

[11] 4,311,463
[45] Jan. 19, 1982

[54] ORTHODONTIC APPARATUS FOR STRAIGHTENING TEETH

[76] Inventor: Albert D. Glattly, 5851 Duluth St., Golden Valley, Minn. 55422

[21] Appl. No.: 178,932

[22] Filed: Aug. 18, 1980

[51] Int. Cl.³ ............................................. A61C 7/00
[52] U.S. Cl. ..................................................... 433/18
[58] Field of Search ................................... 433/18, 20

[56] References Cited
PUBLICATIONS

American Journal of Orthodontics p. 2, vol. 49, No. 5 Apr. 1963.

Primary Examiner—Robert Peshock
Attorney, Agent, or Firm—Wicks & Nemer

[57] ABSTRACT

An orthodontic apparatus for straightening teeth including an arch segment having a base portion, the base portion having a first extension and a second extension spaced from the first extension. A band connected to the arch segment and around a tooth. The ends of the extensions are connected to rubber nodules connected to further rubber nodules mounted on extensions of further arch segments connected to further teeth whereby misaligned teeth are urged to alignment with aligned teeth.

5 Claims, 13 Drawing Figures

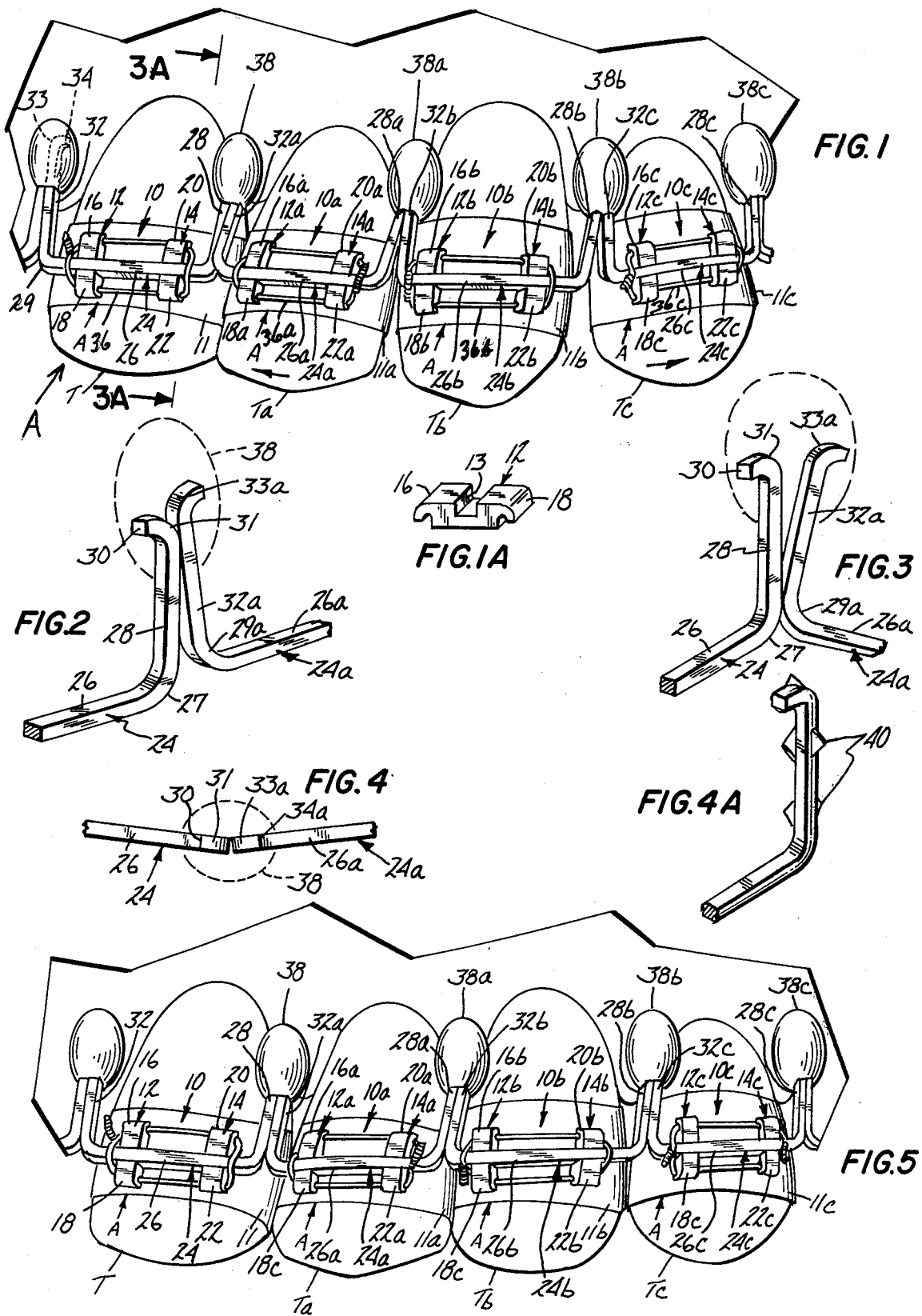

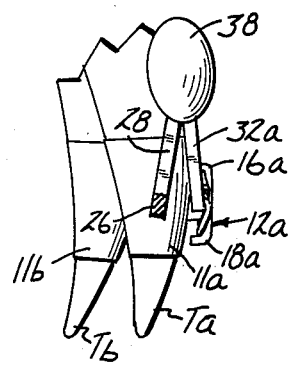
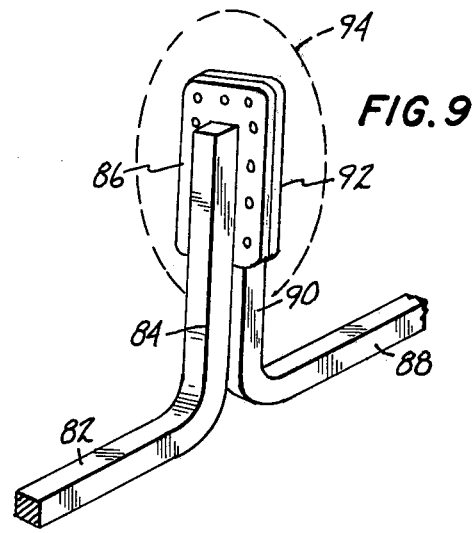
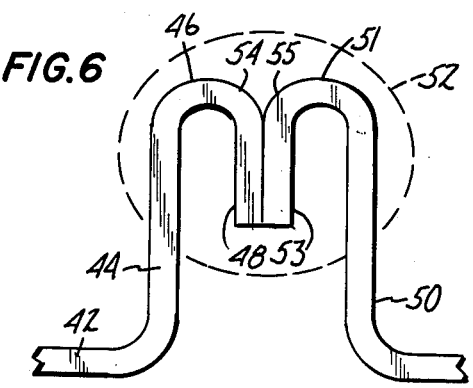
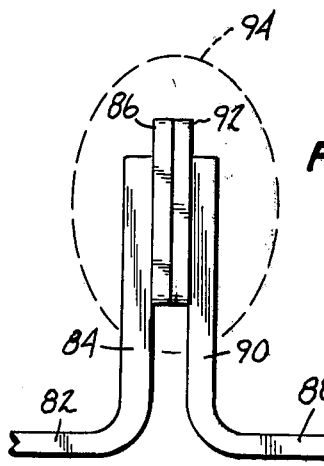
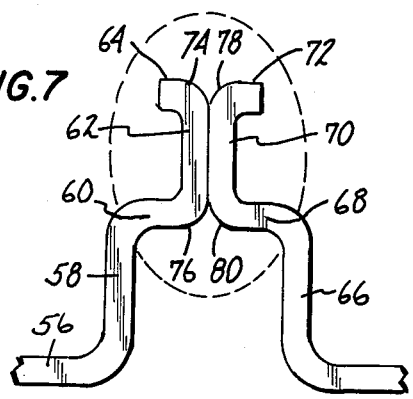
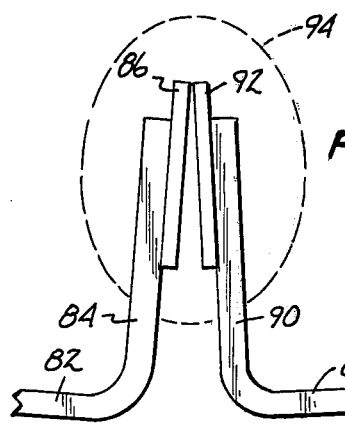

ORTHODONTIC APPARATUS FOR STRAIGHTENING TEETH

SUMMARY

The invention relates to an improvement in orthodontic apparatus for straightening teeth. It appears to be generally conceded that properly aligned teeth provide not only better mastication of food, but also a more desirable facial appearance.

It is an object of the invention to provide an apparatus for straightening teeth which is relatively simple and economically made and which has a continuous and positive action upon the teeth to a final and correct alignment of teeth.

It is a further object of the invention to provide a series of connected segments forming an arch corresponding to the arch of the upper and lower rows of teeth, each segment secured to a tooth. Each segment includes a base portion from which extends first and second spaced extensions, a first extension of a first segment connected to a second extension of a second segment by means of being imbedded in a resilient control nodule together with the second extension of the first segment connected to the first extension of a third segment by means of being imbedded in a resilient control nodule with the segments normally in coplanar relationship, whereby the segments when secured to aligned and misaligned teeth of an arch urge the misaligned teeth to alignment with the arch segments in a normal aligned relationship with aligned teeth.

It is an additional object of the invention to provide an apparatus for correcting teeth alignment whether the teeth protrude, are angularly disposed one way or the other, are vertically off alignment or are separated.

The invention will appear more clearly from the following detailed description when taken in connection with the accompanying drawings, showing by way of example preferred embodiments of the inventive idea wherein like numerals refer to like parts throughout.

In the drawings forming part of this application:

FIG. 1 is a front elevational view of four human teeth with an apparatus for straightening the misaligned teeth mounted thereon and embodying the invention.

FIG. 1a is a perspective view of a conventional bracket.

FIG. 2 is a perspective view of two half portions of an arch segment in opposed corrective abutment positions with the control nodule shown in broken lines.

FIG. 3 is a view similar to FIG. 2 with the arch segments in further corrective positions.

FIG. 3a is a sectional view on the line 3A—3A of FIG. 1.

FIG. 4 illustrates further corrective positions of arch segments.

FIG. 4a illustrates a further embodiment of a leg portion of an arch segment.

FIG. 5 is a view similar to that of FIG. 1 but with the teeth shown in straightened condition.

FIG. 6 is a side view of a further embodiment of the ends of the leg portions of the arch segments and the control nodule.

FIG. 7 is a sectional view of a still further embodiment of that of FIG. 6.

FIG. 8 is a view of an additional embodiment of the ends of the leg portions of arch segments.

FIG. 9 is a perspective view of that illustrated in FIG. 8.

FIG. 10 is a view similar to FIGS. 8 and 9 with the arch segments shown in corrective positions.

Referring to the drawings in detail, the apparatus A for straightening teeth includes the conventional bracket 10 mounted on the tooth T by band 11 with the band secured on the tooth by cement or other conventional means. The bracket 10 further includes a pair of identical spaced conventional bracket portions, 12 and 14, the bracket portion 12 having the tie wings 16 and 18. The bracket portion 14 has the tie wings 20 and 22. The bracket portions 12 and 14 each is formed with a groove 13 having a right angle cross-sectional formation and the bracket portions 12 and 14 are secured by conventional means to the band 11. Three other contiguous teeth are illustrated in FIG. 1 as to Ta, Tb, and Tc and identical apparatus elements are identified by identical reference numerals but accompanied by a lower case letter a, b, or c as the case may be.

The numeral 24 designates a first U-shaped arch segment, a multiplicity of segments making up an arch for the arch formation for each of the upper and lower teeth. The arch segment 24 includes the substantially straight elongated base portion 26 which terminates at one end in an extension in one form of a first right angular leg portion 28. The segment 24 may be made of metal, fiberglass, plastic, or the like. The outer free end of the first leg portion 28 terminates in a protrusion in one form of the hook portion 30 having the curved cam portion 31, the hook overlying the base portion 26. The other end of the base portion 26 terminates in an extension in one form of a second right angular leg portion 32 with the outer free end of the leg portion 32 terminating in a protrusion in one form of the hook portion 34 overlying the base portion 26 and also having a curved cam portion 33 similar to cam portion 31. The base, legs and hooks of the arch segment all lie in the same plane, and the cross section of the arch segment throughout is rectangular. Where the leg portion 28 joins the base portion 26, the curved cam portion 27 is formed and where the leg portion 32 joins base 26, the cam portion 29 is formed.

The base 26 of the arch segment 24 is positioned in the grooves 13 of each of the bracket portions 12 and 14 and secured therein by the tie wire 36 positioned under the tie wings of the bracket portions 12 and 14 and over the base portion 26 of the arch segment and then twisted at the ends and tightened thereby securely mounting the arch segment 24 on the tooth T. Additionally, the base 26 of arch segment 10 or other arch segments may be firmly attached directly to a tooth by a quick hardening cement. With the cross-section of the arch segment base 26 being rectangular and the groove 13 having a right angle cross-sectional formation, together with the wire 36, the arch segment is firmly secured in the bracket portions against displacement.

Additional and identical arch segments are shown, identical portions of which bear identical reference numerals but accompanied by a lower case letter a, b, or c as the case may be.

The outer free ends of the legs 28 and 32a of arch segments 24 and 24a, for example, are securely imbedded by vulcanization or the like in a first substantially egg-shaped control nodule 38 of resilient material such as rubber whereby the arch segment 24 and the arch segment 24a are normally held in alignment in coplanar relationship but which may be distorted but with an urging to normalcy. The hook portion 34 of a leg portion anchors the leg in a nodule so that the leg portion resists rotation and displacement. Arch segment 24b has the leg 32b thereof imbedded by vulcanization in a second nodule 38a with the end of leg 28a of arch segment 24a also imbedded in the nodule 38a. Additionally, the leg 28b of arch segment 24b is imbedded in nodule 38b along with leg 32c of arch segment 24c. The arch segments 24, 24a, 24b and 24c are all held by the nodules in coplanar relationship and which resist movement due to the imbedding of the legs and hooks thereon of the arch segments in the nodules as described. With the cross section of the arch segment rectangular, the same resists rotation within a nodule such as 38 and the hook portion on the ends of the leg portions anchors and prevents displacement of the leg portion from the nodule.

It will be noted in FIG. 1 that tooth Ta is misaligned and protrudes slightly upwardly at the outer portion, and tooth Tc is misaligned and angles to the right, facing FIG. 1. The four arch segments 24, 24a, 24b and 24c together as a unit are secured to the teeth T, Ta, Tb and Tc as in FIG. 1 and in so mounting the unit on the teeth, the arch segment 24a is angled outwardly due to the position of the tooth Ta as mentioned and against the restraining action of the nodule which is always urged to a position of coplanar relationship with the straight arch segments 24 and 24b which are on straight teeth T and Tb. The urging or torqueing effect of the nodules upon the legs of the arch segments to return segments on the misaligned teeth to a coplanar relationship forces the arch segments 24a and 24c and the teeth connected thereto over a period of time to the align with properly aligned teeth T and Tb with all the teeth eventually in alignment. The number of aligned teeth that the segments are mounted on may vary.

Relative to FIG. 2 the position of the arch segment leg 32 is shown as canted due to the mounting of the same on a tooth (not shown) which would urge the leg into the position shown, and it will be seen that the upper end portion of the leg 32a cams on the cam portion 31 of the leg 28 of arch segment 24 to allow ease of and positive corrective movement of the arch segments. Additionally, and with reference to FIG. 3, at the juncture of leg portion 32a and base portion 24a, the cam portion 29a cams on cam portion 27 where in FIG. 3 a misaligned tooth mounted to arch segment 26a would cause the arch segment to initially assume the position of FIG. 3. If there is a change in the vertical relationship of leg 28 and 32a on FIG. 2 because of vertical misalignment of teeth, the nodule will urge and return the legs to a normally aligned condition. If spacing of the teeth completely separates legs 28 and 32a, the nodule will urge and return the legs to their initial aligned relationship thereby closing a space between two teeth. In FIG. 4a the arch segment has the barbs 40 extending from the legs thereof which when imbedded in a nodule resists rotation in and displacement from the nodule due to the barbs.

In FIG. 6 is illustrated a portion of a segment base indicated as 42 which terminates in the leg portion 44. The upper end of the leg portion 44 terminates in the right angular portion 46 terminating in the flange 48 which overlies the leg portion 44. An opposing leg portion 50 of an adjacent arch segment is similarly formed with the right angular portion 51 extending from the leg portion 50 and terminating in the flange 53 overlying the leg portion 50.

The ends of the leg portions 44 and 50 are imbedded by means of vulcanization or the like in control nodule 52 made of a resilient material.

At the juncture of the right angular portion 46 and the flange 48 is the arcuate cam portion 54, and at the juncture of the right angular portion 51 and the flange 53 is the arcuate cam portion 55. The leg portions 50 and 44 may cam on the cam surfaces 55 and 54 somewhat as illustrated in FIG. 2. Additionally, the base 42 of arch segment 10 or other arch segments may be attached directly to a tooth by a quick hardening cement.

In FIG. 7 is illustrated a portion of base 56 which terminates in the leg portion 58 which in turn terminates in the right angular portion 60. The portion 60 terminates in the flange portion 62 parallely disposed to the leg portion 58, and the flange portion 62 terminates in the lip 64. An opposing leg portion 66 of an adjacent arch segment is similarly formed with the right angular portion 68 terminating in the flange portion 70 which in turn terminates in the lip 72.

At the juncture of the flange portion 62 and lip 64 is the arcuate cam portion 74, and at the juncture of the right angular portion 60 and the flange 62 is the arcuate cam portion 76. Additionally at the juncture of the lip 72 with the flange portion 70 is the arcuate cam portion 78 and at the juncture of the right angular portion 68 with the flange 70 is the arcuate cam portion 80. The various cam portions allow camming of the arch segments one upon the other when the segments are misaligned when applied to misaligned teeth.

In FIG. 8 is illustrated a base portion 82 of a segment which terminates in the straight leg portion 84. Connected to the leg portion 82 is the plate 86. Further provided is an opposing base portion 88 which terminates in the straight leg portion 90, and connected to the leg portion 90 is the plate 92 which is the same size as the plate 86. The plates 86 and 92 are in flat contact and in juxtaposition and imbedded in a nodule 94 of resilient material such as rubber, plastic or the like. It will be seen that as the leg portion 84 or leg portion 90 is distorted from the positions shown in FIGS. 8 and 9 in securing the segments to misaligned teeth the plates may cam on either of the vertical edges, and either of the top or bottom edges as viewed in FIGS. 8 and 9 as shown in FIG. 10.

Having thus described the invention, what is claimed as new and desired to be secured by Letters Patent is:

1. Orthodontic apparatus for straightening teeth comprising in combination:
   (a) an arch segment including a base portion,
   (b) said base portion having a first extension and
   (c) a second extension spaced from said first extension,
   (d) means for securing said base portion to a tooth,
   (e) first and second control nodules each of elastic material separate from the material of the arch segment,
   (f) said first extension of said arch segment connected to a second extension of another arch segment by said first extension imbedded at its end portion in said first nodule, and
   (g) said second extension of said arch segment connected to a first extension of another arch segment by said second extension imbedded at its end portion in said second nodule which normally holds said arch segments in coplanar aligned relationship whereby said arch segments when secured to misaligned teeth and aligned teeth urge said misaligned teeth to alignment with said arch segments on aligned teeth to a normal aligned relationship.

2. The apparatus of claim 1 in which said first and second extensions are on opposed sides of said base portion of said arch segment.

3. The device of claim 1 in which the end portion of each extension has a cam surface formed thereon for a cam action with an adjacent extension.

4. The device of claim 3 in which a cam surface is formed at the juncture of an extension with a base portion for a cam action with an adjacent cam surface formed at the juncture of an adjacent extension and base portion.

5. The device of claim 1 in which a cam surface is formed at the juncture of an extension with a a base portion for a cam action with an adjacent cam surface formed at the juncture of an adjacent extension and base portion.

* * * * *